US 11,802,991 B2

United States Patent
Gains et al.

(10) Patent No.: US 11,802,991 B2
(45) Date of Patent: Oct. 31, 2023

(54) SYSTEM AND METHOD FOR PROBABILISTIC ESTIMATION AND DISPLAY OF ATMOSPHERIC GAS DATA AT A GLOBAL SCALE

(71) Applicant: GHGSAT INC., Montreal (CA)

(72) Inventors: David Gains, Montreal (CA); Queeny Shaath, Montreal (CA); Conor McKeen, Montreal (CA); David Green, Montreal (CA)

(73) Assignee: GHGSAT INC., Montreal (CA)

( * ) Notice: Subject to any disclaimer, the term of this patent is extended or adjusted under 35 U.S.C. 154(b) by 0 days.

(21) Appl. No.: 17/765,801

(22) PCT Filed: Oct. 15, 2021

(86) PCT No.: PCT/CA2021/051453
§ 371 (c)(1),
(2) Date: Mar. 31, 2022

(87) PCT Pub. No.: WO2022/077119
PCT Pub. Date: Apr. 21, 2022

(65) Prior Publication Data
US 2023/0119608 A1    Apr. 20, 2023

Related U.S. Application Data

(60) Provisional application No. 63/092,853, filed on Oct. 16, 2020.

(51) Int. Cl.
| | | |
|---|---|---|
| *G01N 33/00* | (2006.01) | |
| *G01W 1/10* | (2006.01) | |
| *G01W 1/00* | (2006.01) | |

(52) U.S. Cl.
CPC ......... *G01W 1/10* (2013.01); *G01N 33/0032* (2013.01); *G01N 33/0047* (2013.01); *G01N 33/0062* (2013.01); *G01N 2033/0068* (2013.01)

(58) Field of Classification Search
CPC ........... G01W 1/10; G01W 1/00; G01W 1/02; G01N 33/0032; G01N 33/0047;
(Continued)

(56) References Cited

U.S. PATENT DOCUMENTS

| | | | | |
|---|---|---|---|---|
| 7,114,388 B1 * | 10/2006 | French | ................ | G01W 1/00 |
| | | | | 73/170.16 |
| 2012/0092649 A1 * | 4/2012 | Wong | ................ | G01W 1/00 |
| | | | | 356/72 |
| 2013/0179078 A1 * | 7/2013 | Griffon | ................ | G01W 1/10 |
| | | | | 702/3 |

(Continued)

FOREIGN PATENT DOCUMENTS

CN    101634711 B  *  6/2013

OTHER PUBLICATIONS

International Search Report and Written Opinion issued by the ISA/CA dated Jan. 12, 2022.
(Continued)

*Primary Examiner* — Jeffrey P Aiello
(74) *Attorney, Agent, or Firm* — Brion Raffoul

(57) ABSTRACT

System and method for estimating how an atmospheric gas is distributed. A server receives prior data related to historical and/or theoretical global patterns of the gas, as well as measurements of the concentration and/or emission of the gas. The server passes the data and measurements to a database for storage and/or to at least one processor, which applies statistical inference methods to estimate a probability distribution of gas concentration and emission within the region. In one embodiment, the entire atmosphere is divided into numerous regions, and gas distributions are evaluated in
(Continued)

each region, to thereby produce an estimated distribution covering the atmosphere. In some embodiments, the regions are divisions of an equirectangular projection of the Earth's surface and have a length and width of 0.025°.

25 Claims, 10 Drawing Sheets

(58) Field of Classification Search
CPC ........... G01N 33/0062; G01N 21/3504; G01N 30/8662; G01N 33/0004; G01N 33/0075; G01N 33/241; Y02P 90/84; Y02P 90/845; Y02A 90/10
USPC ......... 73/23.2, 170.16; 702/1–3, 22–24, 181, 702/188–189; 703/5; 706/12
See application file for complete search history.

(56) References Cited

U.S. PATENT DOCUMENTS

| | | | | |
|---|---|---|---|---|
| 2014/0172323 | A1* | 6/2014 | Marino | G06Q 50/00 702/24 |
| 2021/0255158 | A1* | 8/2021 | Smith | B64D 47/00 |

OTHER PUBLICATIONS

Office Action issued on corresponding Canadian Patent Application No. 3,154,677 dated Feb. 28, 2023. 3 pages.
Notice of Allowance issued on corresponding Canadian Patent Application No. 3,154,677 dated Mar. 27, 2023. 1 page.

* cited by examiner

SYSTEM AND METHOD FOR PROBABILISTIC ESTIMATION AND DISPLAY OF ATMOSPHERIC GAS DATA AT A GLOBAL SCALE

TECHNICAL FIELD

The present invention relates to atmospheric gases. More specifically, the present invention relates to estimating how an atmospheric gas is distributed on a global scale. Further, the present invention relates to displaying and manipulating data related to how an atmospheric gas is distributed at high spatial and temporal resolutions.

BACKGROUND

Climate change, which is fueled in large part by greenhouse gas emissions, has been called "the defining issue of our time" by the United Nations, among others (see https://www.un.org/en/sections/issues-depth/climate-change/). Several atmospheric gases contribute to the 'greenhouse effect', which traps heat within the atmosphere, increasing global temperatures and reducing predictability of weather and climate patterns. Significant world-wide effort has been devoted to slowing climate change and mitigating its effects. These efforts have included multiple national and international commitments to reduce emissions, as well as various actions by individuals.

One of the most significant atmospheric gases in this context is atmospheric methane. Methane passes into the atmosphere from numerous sources, including agriculture and industrial activity, as well as from naturally occurring environmental features such as wetlands. The Environmental Defense Fund, a US non-profit organization, has calculated that approximately 25% of the current manmade warming is due to atmospheric methane.

Despite the urgency of the issues, and the growth of environmental consciousness in industry and the population at large, current climate and chemical transport models only provide low spatial and temporal resolution point estimates of global atmospheric gas concentrations and emissions. In particular, these models resolve gas concentrations and emissions to areas that are hundreds of square kilometres in extent and across a time period that spans hours (or, in some cases, weeks, seasons, or even years) with no formal quantification of uncertainty. Although such broad information can be helpful for regional or national-level policy-making, it is less useful for individual industrial operators or local governments. Systems that provide high resolution estimates of global probability distribution of atmospheric gas (i.e., with resolutions on the order of tens of meters over minutes of time) are clearly needed.

Moreover, the systems that generate current models are typically reliant on specific sources of measurement, e.g., on particular remote instruments or gas emission inventories. Accordingly, these systems cannot easily adapt to new sources of data. A number of remote-sensing missions are anticipated over the next decade, but the data they provide will not be readily assimilated by current systems. Thus, there is a need for systems that can use many different forms of data and that are not necessarily restricted to data from particular instruments.

Additionally, current methods and systems rely on full atmospheric physics models, which require significant input measurements and are computationally expensive. There is a need for models that require less computation effort and comparatively less measurement data. There is also a need for user-friendly display techniques for gas-related data that permit a user to engage with the information provided.

SUMMARY

This document discloses a system and method for estimating how an atmospheric gas is distributed. A server receives prior data related to historical and/or theoretical global patterns of the gas, as well as measurements of the concentration and/or emission of the gas. The server passes the data and measurements to a database for storage and/or to at least one processor, statistical inference methods are then applied to estimate a probability distribution of gas concentration and emission within the region. Data related to the probability distribution can be passed to a display to be displayed to a user (or to another system for later use, such as for simulating and/or forecasting). In one embodiment, the entire atmosphere is divided into numerous regions, and data relating to how the gas is distributed are evaluated for each region, to thereby produce an estimate for how the gas is distributed in the atmosphere. In some embodiments, the display is interactive. In some embodiments, the regions are divisions of an equirectangular projection of the Earth's surface and have a length and width of 0.025°.

In a first aspect, this document discloses a computer implemented method for estimating how a gas is distributed in a geospatial region, the method comprising: identifying a specific region of the Earth's surface; receiving prior data, wherein said prior data is related to at least one of how said gas is previously distributed, a prior concentration, a prior trend, and a prior emission rate for said gas in said specific region; receiving emission data, wherein said emission data is related to an emission rate of said gas is said specific region; and based on said prior data and said emission data, estimating a probability distribution for said gas within said specific region.

In another embodiment, this document discloses a method wherein said distribution is estimated using at least one statistical inference technique.

In another embodiment, this document discloses a method wherein said distribution is estimated using a combination of statistical techniques.

In another embodiment, this document discloses a method wherein said statistical techniques are selected from a group consisting of: a particle dispersion model; a Lagrangian particle dispersion model (LPDM); a chemical transport model (CTM); a global chemical transport model; an inversion technique; and a regional inversion technique.

In another embodiment, this document discloses a method further comprising the step of estimating an inward flow of said gas into said specific region and an outward flow of said gas from said specific region.

In another embodiment, this document discloses a method wherein said inward flow and said outward flow are accounted for when estimating said probability distribution.

In another embodiment, this document discloses a method wherein said specific region is determined based on an equirectangular projection of the Earth's surface.

In another embodiment, this document discloses a method wherein said method is performed for every region in said equirectangular projection, to thereby produce estimates of how said gas is distributed over the atmosphere.

In another embodiment, this document discloses a method further comprising displaying said distribution estimates to a user as an overlay on a map projection of the Earth.

In another embodiment, this document discloses a method wherein said probability distribution is updated in at least one of real time and near real time.

In another embodiment, this document discloses a method wherein said specific region has a length of 0.025° and a width of 0.025°.

In another embodiment, this document discloses a method wherein said gas is methane.

In another embodiment, this document discloses a method wherein said step of estimating said probability distribution is also based on a current concentration measurement of said gas within said specific region, wherein said current concentration measurement is obtained in at least one of real time and near real time.

In another embodiment, this document discloses a method wherein said method is implementable by executing computer-readable and computer-executable instructions encoded on non-transitory computer-readable media.

In a second aspect, this document discloses a system for estimating how a gas is distributed in a geospatial region, said system comprising: a server for: receiving prior data, wherein said prior data is related to at least one of how said gas was previously distributed, a prior concentration, a prior trend, and a prior emission rate for said gas in said specific region; and receiving emission data, wherein said emission data is related to an emission rate of said gas is said specific region; a database for storing said prior data and said emission data; and at least one processor for estimating a probability distribution for said specific region based on said prior data and said emission data and for generating a visual representation for said probability distribution.

In another embodiment, this document discloses a system wherein said probability distribution is converted to a visual representation and wherein said visual representation is displayed to user by overlaying said visual representation on a map projection representing said specific region.

In another embodiment, this document discloses a system wherein said probability distribution is estimated using at least one statistical inference technique.

In another embodiment, this document discloses a system wherein said probability distribution is estimated using a combination of statistical techniques.

In another embodiment, this document discloses a system wherein said statistical techniques are selected from a group consisting of: a particle dispersion model; a Lagrangian particle dispersion model (LPDM); a chemical transport model (CTM); a global chemical transport model, an inversion technique; and a regional inversion technique.

In another embodiment, this document discloses a system wherein said database further contains estimates of an inward flow of said gas into said specific region and an outward flow of said gas from said specific region.

In another embodiment, this document discloses a system wherein said inward flow and said outward flow are accounted for when estimating said probability distribution.

In another embodiment, this document discloses a system wherein said specific region is determined based on an equirectangular projection of the Earth's surface.

In another embodiment, this document discloses a system wherein said method is performed for every region in said equirectangular projection, to thereby produce distribution estimates for said gas over the atmosphere.

In another embodiment, this document discloses a system wherein visual representations of said distribution estimates are overlaid on a map projection of the Earth and displayed on a display.

In another embodiment, this document discloses a system wherein said distribution is updated in at least one of real time and near real time.

In another embodiment, this document discloses a system wherein said specific region has a length of 0.025° and a width of 0.025°.

In another embodiment, this document discloses a system wherein said gas is methane.

In another embodiment, this document discloses a system wherein said user interacts with said display.

In another embodiment, this document discloses a system wherein said probability distribution is further based on a current concentration measurement of said gas within said specific region, wherein said current concentration measurement is obtained in at least one of real time and near real time.

BRIEF DESCRIPTION OF THE DRAWINGS

The present invention will now be described by reference to the following figures, in which identical reference numerals refer to identical elements and in which.

DETAILED DESCRIPTION

The present invention is a system and method for using probabilistic methods to estimate how an atmospheric gas is distributed within the atmosphere. Data related to how the gas was previously distributed and data related to current emissions within a specific geospatial region are gathered from various sources. The gathered data is used as the basis for estimating how the gas is likely distributed within that region. Distributions for multiple regions can then be combined with each other, to thereby produce an estimate for larger areas (up to, in some cases, the entire globe). In some embodiments, statistical inference techniques are used to estimate how the gas is likely distributed. The use of probabilistic and statistical inference methods significantly reduces the computational effort required, when compared to conventional methods. Details of mathematical model(s) that may be used are provided below. However, as would be clear to the person skilled in the art, many different statistical and probabilistic methods may be used to predict and/or determine the gas concentration/distribution for a geographic region, based on historical data and/or current atmospheric/emissions data). Nothing in this description is intended to limit the scope of the invention in any way.

Figure 1:
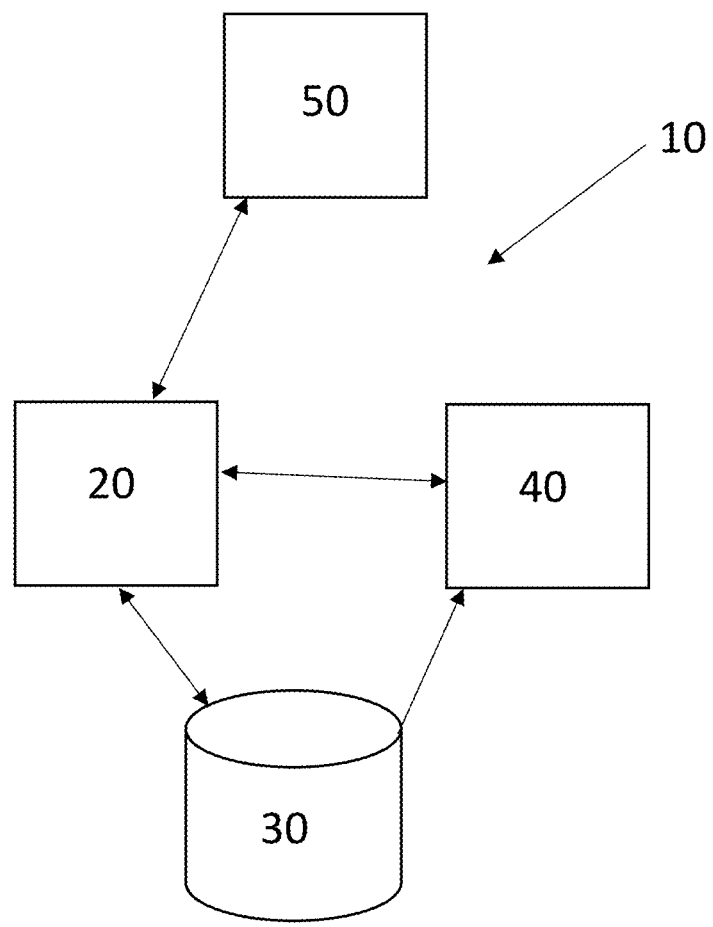
FIG. 1 is a block diagram illustrating a system according to one aspect of the invention.

Referring now to FIG. 1, a system 10 is illustrated according to an aspect of the current invention. A server 20 receives prior data and emission data related to levels of a particular atmospheric gas in a specific geospatial region. These data sets are stored in a database 30. At least one processor 40 then processes the prior data and the emission data using probabilistic methods to estimate a probability distribution of that gas within the region. In one embodiment, an equirectangular projection of the Earth's surface is divided into multiple regions/cells, and a how the gas is distributed for each region/cell is estimated simultaneously or near-simultaneously, to thereby produce an estimate of how that gas is distributed over the entire planet. In some embodiments, the processor 40 also generates a visual representation for the probability distribution. The server 20 can then pass the visual representation and/or other data related to the estimate from the processor 40 to a display 50, which can display the visual representation of analysis results to a user. Of course, in other embodiments, the server 20 can pass data related to the estimate to any suitable system for display or further use. Additionally, in some embodiments, the estimate and/or data related to the estimate is also stored in the database 30 for use with later calculations.

In some embodiments, where the display 50 is a visual display, the display 50 is interactive. For example, the user may be able to zoom in on a particular region of interest in the display, or to zoom out to see how the gas is distributed over larger areas. Further, in some embodiments, a user may use the display to add hypothetical elements to the region and view their probable effects on how the gas is distributed. For instance, in some embodiments, the user may wish to see the probable effects of siting a new factory in a specific region. The user can add a factory having certain emissions characteristics to that region, using the display 50. The server 20 would then pass those characteristics to the processor(s) 40, to be incorporated into how the gas is distributed across the region. Thus, the user could see in real-time, or near real-time, the probable effects of planning decisions on atmospheric gas in the region. As would be understood, various other hypothetical scenarios may be tested using the system 10 in such a manner, including, without limitation, extreme weather events or natural disasters, increased or decreased industrial activity, and increased or decreased motor vehicle activity.

In some embodiments, the display 50 comprises a purpose-built device. In other embodiments, the display 50 comprises a software interface that is made available to a user, either by installation on a computing device operated by the user or by online access through a web portal on such a device.

As mentioned above, in addition or in the alternative to being sent to a display 50, the probability distribution and data related thereto or resulting therefrom can also be sent to a database for further use. The database may be a part of the system 10 or maintained by a third party. In particular, the analysis results of how the gas is distributed may be used to enable technologies for the detection of gas emissions hotspots, which can in turn lead to attribution of emissions to specific sources and/or improved mitigation efforts, as well as improving modelling technologies.

Note that all references herein to a 'geospatial region' or 'geospatial area' are intended to include the atmosphere above that geospatial region/area, as well as the surface. A mathematical representation of such regions/areas will be discussed in more detail below.

The size of the region of interest displayed can be determined by the user. As mentioned above, in some embodiments, the user may choose to examine a larger region or to 'zoom in' on a smaller region of specific interest, for instance above a particular factory or industrial site. The size of each region as processed by the at least one processor 40, however, is preferably small. Independently estimating the probability distribution of many small regions and then displaying those probability distributions over the whole globe allows for greater accuracy than estimating fewer, larger regions would. In one embodiment of the invention, each specific region is of the same size and represents 0.025° of an equirectangular projection of the Earth. This yields results that are relatively "high-resolution" in terms of how gases are distributed in the atmosphere. However, with sufficient processing power, even smaller and more granular regions can be used.

Similarly, the 'temporal resolution' of the data displayed can be determined by the user. For instance, the user may wish to examine how the concentration of gas in a region has changed over a period of time (for instance, over a week, or over several years). Accordingly, in some embodiments, the display is capable of presenting previous data as well as current data, responsive to the user's commands. However, again, the temporal size of the data processed by the at least one processor 40 is preferably small. As with the spatial size, independently estimating the probability distribution at many small-time intervals allows for greater accuracy than estimates at fewer, larger intervals would. In one embodiment of the invention, each time interval is approximately one minute.

Further, in some embodiments, the probability distribution can be updated whenever new data is received. A visual representation of that distribution could be updated at the same time. Alternatively, the probability distribution and/or the visual representation(s) may be updated at a fixed interval, regardless of how often data is received and/or regardless of whether any new information has been received since the last update. In such cases, the fixed updates simulate the propagation of gas according to weather and chemistry, with or without new data, thereby simulating the "movement" of gas regardless of when new data is received. In such cases, the probabilistic estimation approach is useful: as the simulation runs without data, the uncertainty of the concentration and emission estimates grows. When new data is received, the simulation is corrected to match the new data, and the uncertainty in the affected grid cells collapses. Thus, the probabilistic approach allows simulation over short time intervals without receiving data.

Figure 2:
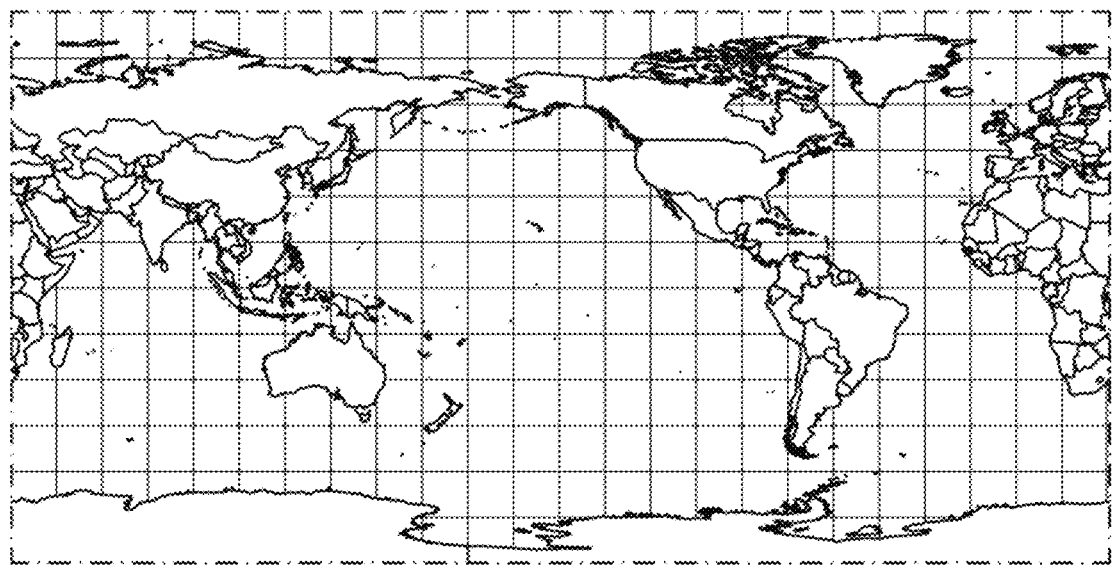
FIG. 2 shows an equirectangular projection of the Earth's surface, according to the prior art.

Note that an equirectangular projection, as shown in FIG. 2, is a cartographic projection in which the Earth's surface is converted to a grid of equal-sized rectangles. Although this projection contains significant distortions when viewed on a global level, the distortions are negligible when dealing with many small areas/regions, as in the high-resolution approach presented by the current invention. Further, in some embodiments, a special case of the equirectangular projection may be used: the plate carée projection, in which the scale is "true" at the equator. There may be advantages to certain projections, depending on the format of the prior data and emission data received. However, as would be clear, any suitable projection may be used depending on the needs of a specific implementation, with suitable mathematical adjustments made as needed.

"Prior data", as used herein, refers to any and all data related to the history of how the gas is distributed within the region of interest. This may include, without limitation, trend data related to seasonal and/or local variation, previous time series model data, and/or data previously measured. As should be understood, prior data may include recent concentration data as well as older data related to concentrations of the gas within the region. This recent concentration data may be collected weeks, days, hours or even minutes before the time of calculation, depending on the implementation. Accordingly, prior data can comprise data related to prior probability distribution(s), prior concentration(s), prior trend(s), and/or prior emission rate(s), and the prior data may be either global or specific to the specific region.

Additionally, in some embodiments. "current concentration data" may be used when estimating the probability distribution. Current concentration data, as used herein, refers to measurements of gas concentrations that are collected at the time of estimation of the probability distribution, in real or near real time. For instance, a monitoring station in the geospatial region could continuously monitor gas concentrations and send that data to the system 10 in real or near real time. As should be clear, "current concentration data" at one time interval may be used as "prior data" for another calculation at a later point. What qualifies as "current concentration data" versus "prior data" can depend on the implementation of the system 10, and specifically on the update frequency selected.

"Emission data" or "emissions data", as used herein, refers to any and all data related to sources of the gas in question within the region. As a non-limiting example, this may include data on the emissions produced by a specific factory, measured at that factory to a high degree of precision. Emission data may also include less-precise data. As another non-limiting example, when the gas in question is methane, the emission data may include the likely emissions of a wetland, determined based on the size and geographic reach of the wetland and of the typical methane emissions of such wetlands. As would be clear, greater precision is generally preferable, but in some cases estimated data may suffice.

Relatedly, depending on the implementation of the system 10, the system 10 may be configured to accept only certain forms of data. However, it may be preferable to allow additional data sources to be included, as research continues and more data become available. Data may be passed to the server 20 by any suitable method, which may depend on the kind of data collected or the data's source. For example, in some cases, data may be directly uploaded to the server 20 by a research team, while in other cases, data may be passed to the server 20 from another database or data aggregation system. Further, the data may include third-party data, including data collected by governments, academic researchers, corporations, and other organizations.

Further, emission data may be gathered directly from one or more sensors in one or more regions of interest. Of course, depending on the type of sensor used, type of data collected, etc., various preprocessing steps may need to be performed to convert the gathered data into data in a format that is suitable for analysis. In practice, each sensor may have a distinct set of preprocessing requirements. The person skilled in the art would be able to implement suitable preprocessing steps for each sensor/data source to be used.

As should also be clear, although the prior data and emission data received by the server 20 relate to the specific region/area in question, they are not restricted to that specific region/area. That is, although some of the data received may relate only to the specific region, other data received may relate to larger regions. For instance, the specific region may comprise a wetland that has particular emissions characteristics, in which case data related to that wetland may be received by the server. Simultaneously, the server 20 may also receive emission data related to the broader geospatial area around that specific region (e.g., state- or country-wide trends). Additionally, as mentioned above, in a preferred embodiment, the system 10 estimates a global probability distribution (by way of estimating probability distributions for each cell independently). The system 10 is preferably configured to determine which pieces of data are relevant to any particular region.

As would be understood by the person skilled in the art, the at least one processor 40 can comprise a single processing unit or many processing units, such as GPUs. The preferred implementation may depend on the form and/or amount of data to be processed. In general, multiple processing units are preferable, as the level of accuracy of the estimated distribution and resulting display increases as more data is processed. Multiple processing units operating in parallel or otherwise in simultaneous operation would be able to process more of the data faster than a single processing unit. In particular, when generating a global display intended to be updated in real or near-real time, multiple processing units are likely preferable, as substantial simultaneous processing would be beneficial. However, the desired implementation for any specific context may be determined by the user.

The system 10 may be configured so that its components communicate in a wired manner, wirelessly, or in a hybrid wired/wireless mode. Among other possibilities, the system 10 may be implemented on the cloud—i.e., in a distributed fashion. The database 30, in particular, may reside on the cloud, or remotely. Similarly, the data processing may be performed by many processing units located in the same physical place or distributed over processing units that are physically remote from each other and/or from the server 20.

Probabilistic Techniques and Examples

Various probabilistic techniques can be used to estimate probability distributions for each geographical location (region). Then, those regional probability distributions can be combined, for example using a well-known or adapted transport model to address emission movements across regional boundaries. Thus, the combination of numerous regional distributions can be used to generate a distribution for larger regions (in some embodiments, covering the entire globe). The use of small regions can nevertheless allow emissions to be resolved to a single source/site.

Recent advances in computing have permitted the use of computer hardware for complex probabilistic computations involving large amounts of data. The following mathematical discussion can be implemented by the system of the present invention to thereby produce a probability distribution of global methane concentration and emission. However, as would be understood by the person skilled in the art, variations on the mathematical approach presented below may equally be implemented. For example, if a gas other than methane were to be considered, the sources considered below would be different. In particular, the proxy densities (defined below) are probabilistic models of the chemical and advective transport of the gas, and thus may be different for different gases. For example, if the gas is methane, proxy distributions could describe how methane is emitted by various processes, moved by wind, and removed from the atmosphere by hydroxyl radicals and dry soil. As another example, if the gas is carbon dioxide, the proxy distributions could describe how carbon dioxide is emitted by various processes, moved by wind, and removed from the atmosphere by photosynthesis and the "ocean sink". However, the statistical inference methods that use these proxy distributions would be applied in the same ways. The person skilled in the art would understand how to adapt the mathematical approach for each relevant gas.

Further, as would be understood, several assumptions underlie the mathematical models given below. As more information related to the behaviour and sources of atmospheric gases become available, the below model may be updated to reflect such new information. In such cases, some of the assumptions presented below may be invalidated, while new assumptions may be added. The current invention should be understood as encompassing any and all such variations. Nothing in this example should be taken as limiting the scope of the invention in any way.

In the following, an interval of time is divided into T nonoverlapping subintervals of equal length. The resulting sequence of subintervals is indexed by the variable t=1, . . . , T and the value of a time-dependent variable X averaged over the t-th subinterval is written $X_t$. For the sake of efficiency, this variable may be described as "X at time t". While the methods described do not depend on a particular subinterval length, in practice it can be fixed to approximately one minute.

Methane is assumed to be emitted by objects and structures on the Earth's surface nonuniformly in both space and time. The model for these emissions is a sequence $\rho_1, \ldots, \rho_T$ of variables such that for each t=1, . . . , T:

(1) $\rho_t$ is a two-dimensional regular grid that covers a plate carée projection of the Earth's surface.
(2) each cell of the grid $\rho_t$ has an extent of 0.025°×0.025°.
(3) the value of the (i,j)-th grid cell of $\rho_t$, in symbols $\rho_t(i,j)$, is the earth's surface methane emission rate averaged over the cell over the t-th time interval. The unit of emission rate $\rho_t(i,j)$ is mass/area/time.

Similarly, the mass of methane in the earth's atmosphere is modeled as a sequence $m_1, \ldots, m_T$ of three-dimensional regular grids such that for each t=1, . . . , T:

(1) the horizontal dimensions of $m_t$ cover a plate carée projection of the Earth's surface;
(2) each cell of the grid $m_t$ has an extent of 0.025°×0.025°×1 km; and
(3) the value of the (i,j,k)-th grid cell of $m_t$, in symbols $m_t(i,j,k)$, is the mass of atmospheric methane averaged over the cell over the t-th time interval.

Also associated with each t=1, . . . , T is a data vector $Z_t$ which comprises measurements or observations of gas concentration or emission acquired over the t-th time interval (which may comprise "concentration data", "prior data" and/or "emission data", as defined above). Note that the vector $Z_t$ can be empty in the case where no relevant data is acquired over the t-th time interval.

For each t=1, . . . , T, the posterior probability distribution of the mass grid $m_t$ and the emission rate grid $\rho_t$, given all accumulated data $Z_{1:t}$, is estimated. The following assumptions constrain the estimation:

(1) the cells of the grid $m_t$ are independent of each other;
(2) the cells of the grid $\rho_t$ are independent of each other;
(3) the methane mass $m_t(i,j,k)=0$ when cell (i,j,k) lies above the atmosphere;
(4) the methane mass $m_t(i,j,k)=0$ when cell (i,j,k) lies below the earth's surface;
(5) the methane mass $m_t(i,j,k)$ depends on the emission rate grid $\rho_t$ (specifically, on the emission rate $\rho_t(i,j)$) if and only if the cell (i,j,k) intersects both the earth's surface and the atmosphere;
(6) for any time index t, the elements of the data vector $Z_t$ are independent of each other; and
(7) for any time index t, the data vector $Z_t$ depends only on $m_t$ and $\rho_t$.

It follows from assumptions (1) and (2) that the density $p(m_t, \rho_t | Z_t)$ of the posterior distribution of interest can be written as follows:

$$p(m_t, \rho_t \mid Z_{1:t}) = \prod_{(i,j,k)} p(m_t[i,j,k] \mid \rho_t, Z_{1:t}) \prod_{(i,j)} p(\rho_t[i,j] \mid Z_{1:t})$$

Furthermore, it follows from assumptions (3), (4) and (5) that:

For grid cells (i,j,k) that lie above the atmosphere or below the earth's surface, the methane mass $m_t(i,j,k)$ is deterministically 0, i.e.

$$p(m_t[i,j,k] \mid \rho_t, Z_{1:t}) = \mathrm{Dirac}(m_t[i,j,k])$$

For grid cells (i,j,k) that intersect both the earth's surface and the atmosphere, the methane mass density is $$p(m_t[i,j,k] \mid \rho_t, Z_{1:t}) = p(m_t[i,j,k] \mid \rho_t[i,j], Z_{1:t})$$

For grid cells (i,j,k) that lie above the earth's surface and in the atmosphere, the methane mass density is $$p(m_t[i,j,k] \mid \rho_t, Z_{1:t}) = p(m_t[i,j,k] \mid Z_{1:t})$$

A notational convenience may be used to simplify the explanation provided. For grid cells (i,j,k) that intersect both the earth's surface and the atmosphere, the symbol $X_t[i,j,k]$ denotes the mass and emission rate pair $(m_t[i,j,k], \rho_t[.,j])$. For grid cells (i,j,k) that lie above the earth's surface and in the atmosphere, the symbol $X_t[i,j,k]$ identifies the mass $m_t[i,j,k]$.

To estimate the posterior probability distribution of the mass grid $m_t$ and the emission rate grid $\rho_t$ given all accumulated data $Z_{1:t}$ for each time interval t, and from assumptions (1) through (5) and the definition of $X_t[i,j,k]$, it is sufficient to estimate the independent posterior probability distributions of $X_t[i,j,k]$ given the accumulated data $Z_{1:t}$ for each time interval t and each grid cell (i,j,k).

Note that exact inference of the posterior distributions $X_t[i,j,k] | Z_{1:t}$ is infeasible. However, useful estimates can still be obtained via the well-known technique of "marginal particle filtering" (MPF). The marginal particle filter is a statistical inference technique that estimates the posterior distribution of each $X_t[i,j,k]$ given $Z_{1:t}$ via a set of N weighted samples, or "particles". In the following, the samples are denoted $X_t^1[i,j,k], \ldots, X_t^N[i,j,k]$ and their corresponding weights are denoted $w_t^1[i,j,k], \ldots, w_t^N[i,j,k]$ respectively. A property of the MPF estimate is that any statistic of the posterior distribution of $X_t[i,j,k]$ is approximated by the corresponding sample statistic, and the distance between the statistic and its approximation approaches 0 as N approaches infinity. For example, the mean $\overline{X}_t[i,j,k]$ of $p(X_t[i,j,k]|Z_{1:t})$ is approximated by the weighted sample mean $$\hat{X}_t[i,j,k] = \sum_{n=1}^{N} w_t^n[i,j,k] X_t^n[i,j,k] \text{ and}$$

$$\hat{X}_t[i,j,k] \to \overline{X}_t[i,j,k] \text{ as } N \to \infty.$$

The MPF technique relies on assumptions (6) and (7) above and can be described by the following steps:

for n=1, ..., N, determine sample $X_t^n[i,j,k]$ from a proxy distribution $q(X_t^n[i,j,k])$
for n=1, ..., N, determine the weight $\tilde{w}_t^n[i,j,k]$ as follows:

$$\tilde{w}_t^n[i,j,k] = \frac{p(Z_t | X_t^n[i,j,k]) \int p(X_t^n[i,j,k] | m_{t-1}, \rho_{t-1}) p(m_{t-1}, \rho_{t-1} | Z_{1:t-1}) dm_{t-1}, \rho_{t-1}}{q(X_t^n[i,j,k])}$$

and normalize the weights $\tilde{w}_t^{1:N}[i,j,k]$ to obtain $w_t^{1:N}[i,j,k]$.

Once the transitional prior densities $p(X_t^n[i,j,k]|m_{t-1}, \rho_{t-1})$ have been specified, the integrals in the weight calculations can be approximated by computing appropriate sums over the samples $X_{t-1}^{1:N}[i',j',k']$ and weights $w_{t-1}^{1:N}[i',j',k']$ generated by the MPF for all grid cells (i', j', k') over the (t−1)-th time interval. The MPF is thus a recursive algorithm that provides sequential, real or near real-time updates of mass and emission rate grid cells at fixed simulation time steps or, in other embodiments, whenever new data is acquired. Moreover, the MPF technique can accommodate arbitrary models (e.g., non-Gaussian models), and can be validated using various validation schemes, including, without limitation, Bayesian model checks derived from the posterior predictive distribution.

It should be noted that, while the $X_t[i,j,k]$ are independent for all grid cells (i,j,k), each $X_t[i,j,k]$ does depend on all cells of the mass and emission rate grids $m_{t-1}$ and $\rho_{t-1}$. This "link to the past" is demonstrated by the MPF weight calculation.

The MPF technique requires the following to be specified for each t=1, ..., T and for each grid cell (i,j,k):
1. likelihoods $p(Z_t|X_t[i,j,k])$;
2. transitional priors $p(X_t[i,j,k]|m_{t-1}, \rho_{t-1})$; and
3. proxy distributions $q(X_t[i,j,k])$.

Each will be discussed in more detail below.

Likelihoods

The likelihood densities are probabilistic models of the processes that generate measurements of atmospheric gases (e.g., models of the action of satellite-based instruments, etc.). Thus, the likelihood models depend on the number and type of measurement sources. The measurements $Z_t$ are assumed to be distributed over a 2D grid with a structure identical to that of $\rho_t$. A typical methane measurement $Z_t[i,j]$ is either empty or consists of a retrieved methane concentration $c_t[i,j]$ and a retrieved albedo $a_t[i,j]$. When the retrieval is "artefact free", the measurement can be written as:

$$c_t[i,j] = f(m_t[i,j,1], \ldots, m_t[i,j,K]) + \epsilon_t[i,j]$$

where the function $f$ converts the sum of its input masses to a mole fraction concentration, K is the number of layers of the mass grid and $\epsilon_t[i,j]$ is a zero mean Gaussian noise with standard deviation $\sigma_t[i,j]$. The resulting artefact-free likelihood density function is thus:

$$p(Z_t | m_t) = \prod_{(i,j)} \text{Normal}(Z_t; f(m_t[i,j,1], \ldots, m_t[i,j,K]), \sigma_t[i,j])$$

It should be noted that this model is ideal and does not account for all data. For instance, methane concentrations retrieved from the TROPOspheric Monitoring Instrument (more commonly called TROPOMI, a European-managed satellite-mounted instrument) have a nontrivial relationship with albedo which is not encoded by this artefact-free model. Again, the precise models and mathematical relations used by the system will depend on the data received, and suitable models can be selected for that data by the skilled user.

Transitional Priors

In general, the transitional priors have the following form:

$$p(X_t[i,j,k]|m_{t-1},\rho_{t-1}) = p(m_t[i,j,k]|\rho_t[i,j,k],m_{t-1},\rho_{t-1})p(\rho_t[i,j,k]|m_{t-1},\rho_{t-1})$$

Then, assuming that the methane masses and emission rates are autoregressive (i.e., each variable is linearly dependent on its previous values and a stochastic term), and that the time interval is relatively short, the transitional prior $$p(m_t[i,j,k]|\rho_t[i,j,k],m_{t-1},\rho_{t-1}) = p(m_t[i,j,k]|m_{t-1}[i,j,k])$$

can be chosen normal with mean $m_{t-1}[i,j]$ and $$p(\rho_t[i,j]|m_{t-1},\rho_{t-1}) = p(\rho_t[i,j]|\rho_{t-1}[i,j])$$

can be chosen normal with mean $\rho_{t-1}[i,j]$.

Proxy Distributions

The proxy distributions are predicated on models that describe the inflow and outflow of the gas to the region. In particular, models informing the choice of proxy distribution for a methane mass would include terms representing the mass gained from advection, the mass lost by advection, the mass lost to absorption by dry soil (which will be zero in grid cells that do not intersect the Earth's surface), and the mass lost to reactions with hydroxyl radicals, among others.

The proxy distributions for emission rates are derived from emissions inventories produced by third parties. These inventories describe the emission rates of, e.g., activities related to oil and gas production, wetlands, oceans and other emitters.

For each t=1, ..., T, let $c_t$ be a grid of gas concentrations such that the cell structure of $c_t$ is identical to that of the emission rate grid $\rho_t$. The distribution of the concentration grid $c_t$ is determined from the estimated posterior distribution of the mass grid $m_t$, given data $Z_{1:T}$, as follows. First, for each 3D grid cell (i,j,k), a normal distribution $G_t[i,j,k]$ of masses is fit to each set of samples $X_t^{1:N}[i,j,k]$ and weights $w_t^{1:N}[i,j,k]$ generated by the MPF. Next, for each 2D grid cell (i,j), a normal distribution $G_t[i,j]$ of the total mass of gas above the cell is determined by summing the normal variates $G_t[i,j,1:K]$. Finally, $G_t[i,j]$ is scaled to a distribution of mole fraction concentrations to obtain the distribution of concentrations $c_t[i,j]$.

However, as should be understood, many different statistical techniques may be used by embodiments of the present invention. Although the MPF technique described may be suitable for certain implementations, nothing in the description of this specific mathematical approach should be considered to limit the invention in any way. For instance, well-known techniques such as sequential variational inference (SVI) can be used in certain implementations and should be also understood as forming part of the present invention.

Regional Inversions Model Embodiment

In another embodiment, "regional inversions" are used to estimate probability distributions within specific regions. In combination with a chemical transport model (i.e., CTM) as further described below, the regional inversions for each region can be combined to provide estimate for larger geographic areas (up to, if a global CTM is used, the entire globe). That is, the approach detailed below combines several models and techniques, including a dispersion model, a transport model, and regional inversions, to thereby produce an estimate of how a gas is distributed over large areas or the entire globe. However, as noted above, many different statistical techniques may be used by embodiments of the present invention. Nothing in the description of this specific mathematical approach should be considered to limit the invention in any way.

In this embodiment, a set E of potential GHG emitters is known. For example, if the GHG is methane and the set is representative of the world's potential methane emitters, then E could include oil and natural gas extraction, processing, and transport facilities, landfills, ruminant farming systems, termite mounds, wetlands, etc. The 'emission rate estimator' (i.e., the system of the present invention) determines and tracks GHG emissions from each of the potential emitters of E in near real time.

Figure 3:
FIG. 3 shows the location of potential emitters in a region of Algeria.

In this embodiment, the set of potential GHG emitters E is partitioned according to a regular grid over a plate carrée projection of the Earth's surface. Each grid cell containing at least one emitter is called a region. For example, FIG. 3 shows potential methane emitters in a region that covers part of Algeria. Each dot on this image indicates the location of a potential emitter/emission source.

In general, direct measurements of GHG emission from any one of the potential emitters in the set E are not available. Hence the emission rate estimator model infers GHG emissions from column averaged GHG concentration measurements. These measurements are retrieved from hyperspectral and multispectral images generated by remote sensing platforms, which may include third-party and proprietary sensing platforms such as TROPOMI, the Japanese Greenhouse Gases Observing Satellite (GOSAT), NASA's Orbiting Carbon Observatory-2 (OCO-2) and Orbiting Carbon Observatory-3 (OCO-3), the European Sentinel-2 satellite platform, the Italian Space Agency's PRISMA platform, Landsat 8 and/or other systems managed by the US Geological Survey and other US or foreign government organizations, the non-governmental MethaneSAT, and other constellations of satellites and aircraft.

Measurements

In this embodiment, for each $t=1, \ldots, T$, let $z_t$ be a set of measurements. In detail, the j-th element of $z_t$ is a triple $z_t^j = (c_t^j, B_t^j, \epsilon_t^j)$, where $c_t^j$ is a column averaged GHG concentration measurement (units mol/m$^2$);

$B_t^j$ is the projection of the column boundary onto the surface of the earth; and $\epsilon_t^j$ is a measurement error (units mol/m$^2$).

Figure 4:
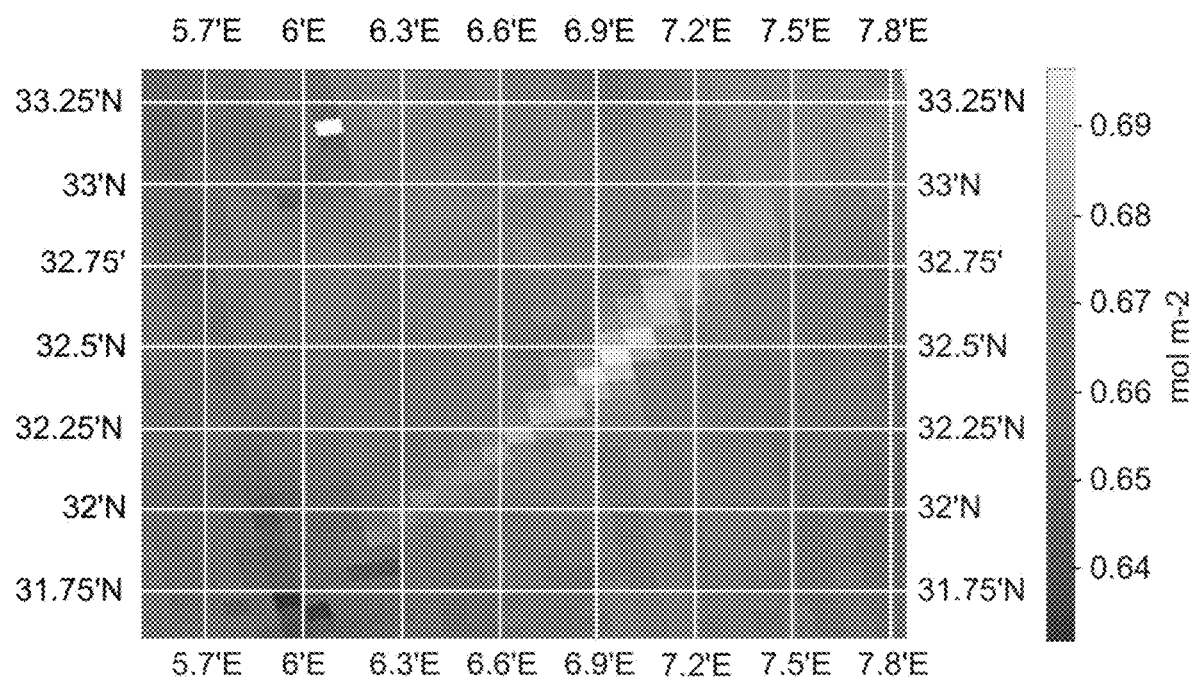
FIG. 4 shows an exemplary set of column averaged GHG concentration measurements.

$B_t^j$ can also be referred to as the measurement footprint or the pixel. It is assumed that the area of such a pixel can be calculated and is denoted A). FIG. 4 shows a set of column averaged GHG concentration measurements retrieved from a TROPOMI image on Jan. 4, 2020.

Thus, for each $t=1, \ldots, T$ and each $i=1, \ldots, N$, the emission rate estimator produces an estimate of the rate $\rho_i(t)$ at which the GHG is emitted from the point $e_i$ over the time interval $(t-1, t]$, and the estimates are computed from the measurements $z_t$.

Model Overview

The emission rate estimator model of this embodiment comprises a collection of 'regional inversions' supported by a 'dispersion model' and a global chemical transport model (CTM). A single regional inversion $I(R, t)$ is associated with each region R and each time interval $(t-1, t]$. Specifically, $I(R, t)$ produces emission rate estimates for each potential emitter in the region R over the time interval $(t-1, t]$.

Suppose there are N potential GHG emitters in E. Their locations on the surface of the earth are denoted $e_1, \ldots, e_N$ respectively. $t=0, \ldots, T$ be a discrete index of time such that time t occurs strictly before time t+1 for all t<T. For each $i=1, \ldots, N$ and each $t=1, \ldots, T$, the rate at which the GHG is emitted from the i-th potential emitter in the time interval $(t-1, t]$ is denoted $\rho_i(t)$. Units of GHG emission rate are of the form mass per unit time, e.g., kg/s, t/h, etc.

For any $t=1, \ldots, T$, consider the time interval $(t-1, t]$. Column averaged GHG concentrations that arise from emissions produced by the emitters of E in the time interval $(t-1, t]$ are called enhancements. GHG concentrations that arise from other emissions are called background. The dispersion model estimates the spatial distribution of enhancement while the global chemical transport model estimates background concentrations. Regional inversions operate on both estimates. The dispersion model, global chemical transport model and regional inversions are described below.

Dispersion Model (LPDM)

Regional inversions depend on a Lagrangian particle dispersion model (LPDM) that describes the propagation of GHG emission over time and space. Any LPDM that satisfies certain requirements, enumerated below, would be compatible with the emission rate estimator's regional inversions. The operation and output of any compatible LPDM is explained to facilitate the description of regional inversions. The person skilled in the art can determine a suitable LPDM for any specific implementation.

For any $t=1, \ldots, T$, the time interval $(t-1, t]$ can be divided into S subintervals of equal length $\Delta t$. For each $s=1, \ldots, S$, the LPDM accounts for a newly released particle (which may be represented in the LPDM as a 'tracer' value) from each emitter location $e_1, \ldots, e_N$, and updates location values of previously released tracers (i.e., as particles previously released move through the atmosphere).

Each tracer released by the LPDM represents a mass of GHG emitted over $\Delta t$ units of time. To update the location of a tracer, the LPDM moves the tracer according to wind and the value of other atmospheric variables over the time interval $(t-1, t]$. These atmospheric variables may be obtained from a third-party database, data centre, or data system, such as the well-known Goddard Earth Observing System (GEOS) operated by the US NASA, or the well-known European Centre for Medium-Range Weather Forecasts. Such variables may be forecasted or near-real-time, as desired.

Regional inversions operate on tracers in the tracer's 'final state', i.e., a tracer's location after a certain predetermined number of iterations of the LPDM. In some embodiments, the 'final state' may be taken as the tracer's location after five iterations. However, as should be clear, the person skilled in the art can select any suitable number of iterations for the desired implementation.

Suppose after S iterations there are M tracers. The location of the i-th tracer is then assumed to be normally distributed with mean $\mu_i=(x_i, y_i, z_i)$ and xy-covariance parameters $\Sigma_i=(\sigma_i^x, \sigma_i^y, r_i)$, such that the covariance of the i-th tracer's horizontal location is given by $$\begin{bmatrix} \sigma_i^x \sigma_i^x & \sigma_i^x \sigma_i^y r_i \\ \sigma_i^x \sigma_i^y r_i & \sigma_i^y \sigma_i^y \end{bmatrix}$$

It follows that $0<\sigma_i^x$, $\sigma_i^y$ and $-1 \leq r_i \leq 1$. As such, the LPDM satisfies the following requirements for compatibility with regional inversions:

the LPDM accommodates a fixed timestep $\Delta t$; and
the LPDM propagates both the mean and covariance of tracer location.

Figure 5:
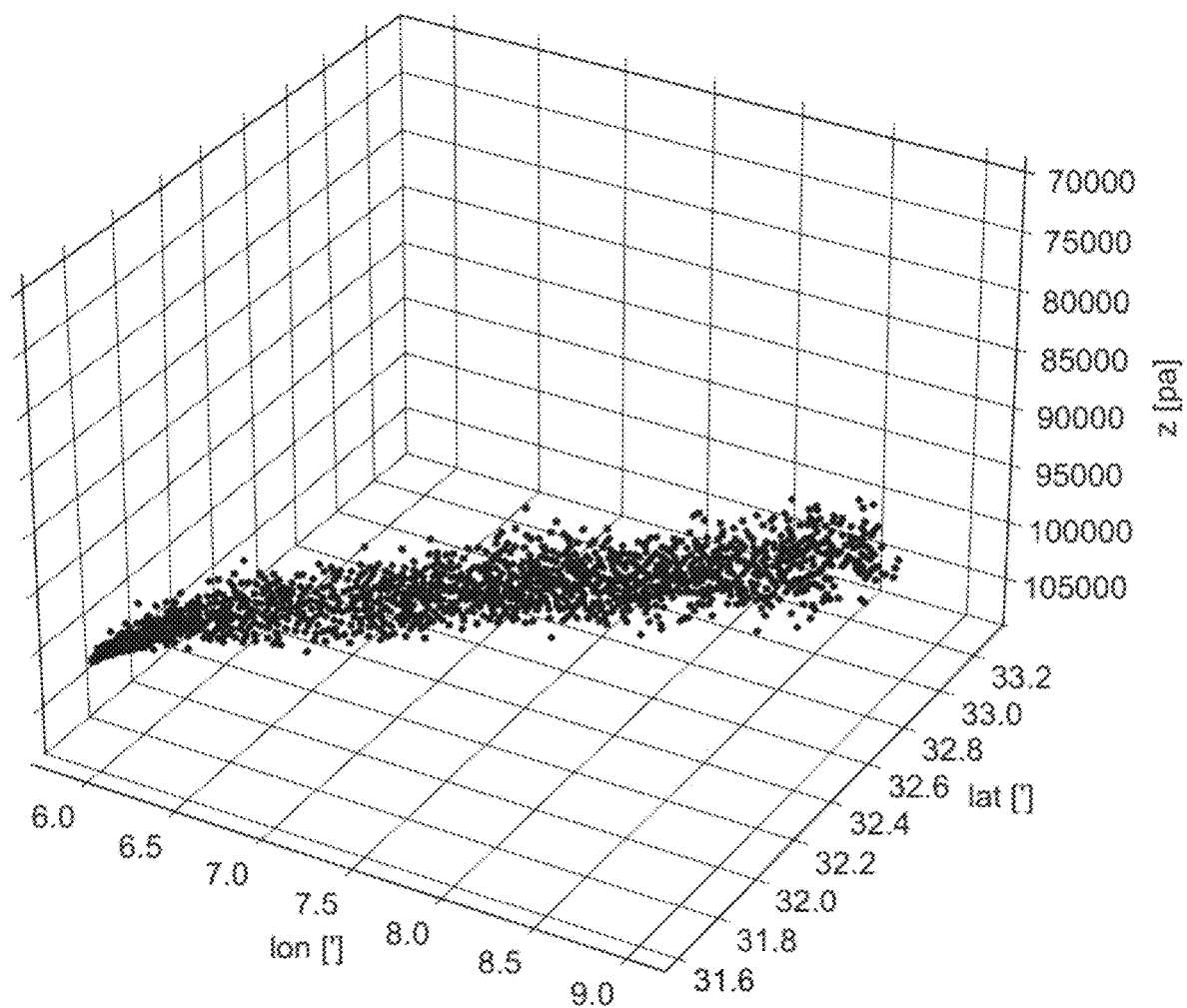
FIG. 5 shows the mean location of tracers generated by a particle dispersion model, according to one implementation of the invention.

As an example, FIG. 5 shows the mean location of tracers generated by an LPDM simulating emissions from a single point in Algeria. This plot shows the final state of a set of tracers (in terms of longitude, latitude, and height in the atmosphere in term of pressure) according to an LPDM which was run for S=3600 iterations, with $\Delta t$=13 seconds.

Global Chemical Transport Model (CTM)

For each t=1, ..., T, the global chemical transport model (CTM) produces a field $b_t$ such that for each point (x, y) on the surface of the Earth, $b_t(x,y)$ is the column averaged background concentration of the GHG at (x,y) averaged over the time interval (t−1, t]. To compute the background fields $b_{1:T}$, the CTM operates on the concentration measurements $z_t$ and the output of regional inversions.

Regional inversions are compatible with well-known CTMs such as the GEOS-Chem CTM, but other CTMs, such as the well-known TM5 atmospheric chemistry model can also be adapted for use with the methods described herein. The person skilled in the art would be able to adapt a CTM for suitable analysis.

Regional Inversions

Let R be a region as defined above (i.e., a cell of a regular grid over a plate carrée projection of the Earth's surface that contains at least one emitter from the set E). Then, suppose that R contains $N_R$ potential GHG emitters. Reindexing the set of emitters for each t=1, ..., T, their locations and emission rates can be written as $e_1$, ..., $e_N$, and $\rho_1(t)$, ..., $\rho_{N_R}(t)$ respectively.

Then, for any given t, it can be assumed that the LPDM has generated M tracers $(\mu_1, \Sigma_1^0)$, ..., $(\mu_M, \Sigma_M^0)$, each one released from one of the emitters in the region, and that the CTM has produced the background concentration field $b_{t-1}$. The regional inversion I(R, t) determines the joint posterior probability distribution of emission rates $\rho_{1:N_R}(t)$ and tracer covariances $\Sigma_{1:M}$ given $(\mu_{1:M}, \Sigma_{1:M}^0)$, $b_{t-1}$ and K column averaged GHG concentration measurements $z_t^{1:K}$.

The joint posterior distribution is unknown. However, its density function can be computed up to proportionality, as follows:

$$p(\rho_{1:N_R}(t), \Sigma_{1:M} | z_t^{1:K}, \mu_{1:M}, \Sigma_{1:M}^0, b_{t-1}) \propto p(\rho_{1:N_R}(t), \Sigma_{1:M}) p(z_t^{1:K} | \rho_{1:N_R}(t), \mu_{1:M}, \Sigma_{1:M}, b_{t-1}) \quad (1)$$

Then, assuming independence of measurements, the likelihood (right-most factor of (1)) can be further factored as $$p\left(z_t^{1:K} \middle| \rho_{1:N_R}(t), \mu_{1:M}, \sum\nolimits_{1:M}, b_{t-1}\right) = \prod_{k=1}^{K} p\left(z_t^k \middle| \rho_{1:N_R}(t), \mu_{1:M}, \sum\nolimits_{1:M}, b_{t-1}\right) \quad (2)$$

It is thus sufficient to define a single factor, for example the k-th, of the likelihood. The density of such a factor is determined by the measurement model for the sensor generating $z_t^k$. However, a simple normal measurement model is often assumed. To define this model, first define the "true" GHG enhancement in the k-th pixel as $$\delta_t^k = \frac{1}{mA_t^k} \sum_{i=1}^{M} \int_{B_t^k} \rho(t, i) \Delta t p\left(x, y \middle| \mu_i, \sum\nolimits_i\right) dx dy \quad (3)$$

In equation (3), $\rho(t, i)$ is the emission rate of the emitter that released the i-th tracer, and m is the molar mass of the GHG. The measured GHG enhancement in the k-th pixel can then be written as $$\tilde{c}_t^k = c_t^k - \int_{B_t^k} b_{t-1}(x, y) dx dy \quad (4)$$

Then, (3) and (4) can be combined to obtain the likelihood density of the k-th measurement:

$$p(z_t^k | \rho_{1:N_R}(t), \mu_{1:M}, \Sigma_{1:M}, b_{t-1}) = \text{Normal}(\tilde{c}_t^k; \delta_t^k, \epsilon_t^k) \quad (5)$$

The prior density on emission rates and tracer covariances in (1) is assumed to factor as:

$$p(\rho_{1:N_R}(t), \Sigma_{1:M}) = \prod_{i=1}^{N_R} p(\rho_i(t)) \prod_{j=1}^{M} p(\Sigma_j) \quad (6)$$

According to the law of total probability, the prior density on each emission rate factor is thus $$p(\rho_i(t)) = \int p(\rho_i(t) | \rho_i(t-1)) p(\rho_i(t-1)) d\rho_i(t-1) \quad (7)$$

Emission rates estimated for the previous time interval (t−2, t−1] thus inform estimates at the current time interval (t−1, t]. The form of the transitional density $p(\rho_i(t)|\rho_i(t-1))$ can be assumed to be lognormal. Lognormal parameters can be adjusted according to what is known historically about the i-th potential emitter. The prior $p(\rho_i(t-1))$ is taken to be the posterior density of emission rate estimated at the previous time interval. The prior density on each tracer covariance factor $p(\Sigma_j)$ is $$p(\Sigma_j) = p(\sigma_j^x) p(\sigma_j^y) p(r_j) \quad (8)$$

The density $p(r_j)$ is uniform on the interval $[-1,1]$. The density on each standard deviation $\sigma_j = \sigma_j^x$, $\sigma_j^y$ of is InverseGamma($\alpha_j, \beta_j$) with $\alpha_j = S_j/2$ and $\beta_j = \alpha_j \sigma_j^0$ where $S_j$ is the "age" of the j-th tracer, i.e., the number of iterations the tracer has been updated by the LPDM, and $\sigma_j^0$ is the relevant component of the covariance $\Sigma_j^0$ calculated by the LPDM.

Inference

The regional inversion I(R, t) provides an empirical estimate of the joint posterior probability distribution of emission rates $\rho_{1:N_R}(t)$ and tracer covariances $\Sigma_{1:M}$ given an initial tracer configuration $(\mu_{1:M}, \Sigma_{1:M}^0)$, a background concentration field $b_{t-1}$ and concentration measurements $z_t^{1:K}$. In other words, the posterior estimate is a collection of L samples drawn from the posterior itself such that sample statistics computed on the estimate approach statistics of the true posterior as $L \to \infty$.

The L samples $(\rho_{1:N_R}^1(t), \Sigma_{1:M}^1)$, ..., $(\rho_{1:N_R}^L(t), \Sigma_{1:M}^L)$ are generated by a Markov chain Monte Carlo (MCMC) algorithm, specifically a preconditioned stochastic gradient Langevin dynamics (pSGLD) algorithm. This sampler was chosen rather than e.g., Hamiltonian MCMC, because the dimension of the sample space in the pSGLD algorithm is comparatively high. However, of course, any suitable algorithm (not limited to MCMCs or other Monte Carlo methods) can be used, as would be clear to the person skilled in the art.

The pSGLD sampler used in this implementation is driven by K cost functions of the form $$g_k(\rho_{1:N_R}(t), \Sigma_{1:M}) = -\log(p(\rho_{1:N_R}(t), \Sigma_{1:M}) p(z_t^k | \rho_{1:N_R}(t), \mu_{1:M}, \Sigma_{1:M}, b_{t-1})) \quad (9)$$

Then, for a normal measurement model, the cost functions (9) can be written $$g_k\left(\rho_{1:N_R}(t), \sum_{1:M}\right) = \frac{1}{2}\left(\frac{\tilde{c}_t^k - \delta_t^k}{\epsilon_t^k}\right)^2 + \log(\epsilon_t^k\sqrt{2\pi}) - \log\left(p\left(\rho_{1:N_R}(t), \sum_{1:M}\right)\right) \quad (10)$$

Assuming the l-th sample $(\rho_{1:N_R}^l(t), \Sigma_{1:M}^l)$ has been generated, the pSGLD sampler draws the (l+1)-th sample via the following procedure:

1. Sample $k$ from $1, \ldots, K$

Figure 6:
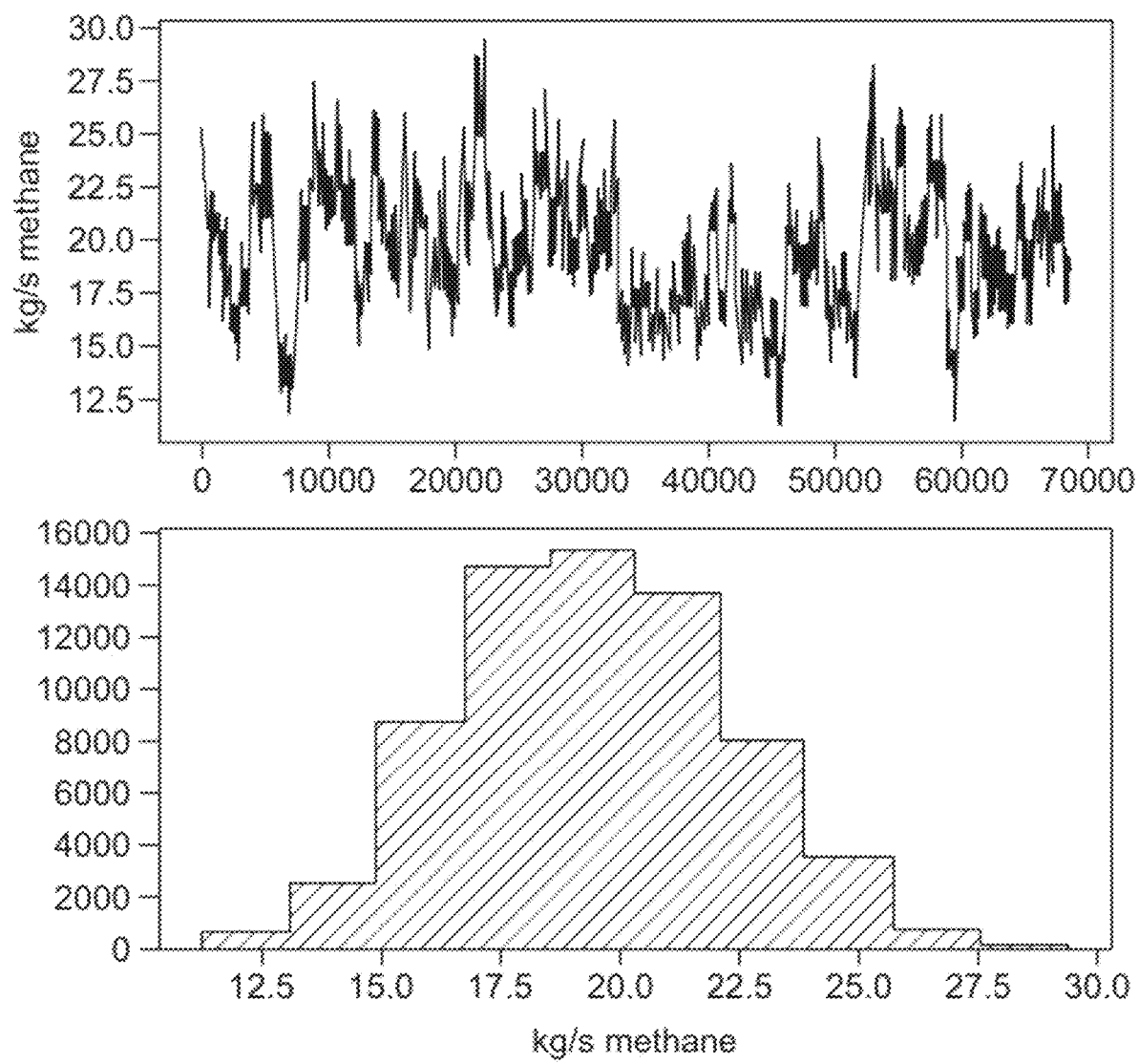
FIG. 6 shows samples of emission rate associated with a single emitter and a corresponding empirical posterior distribution.

2. $\text{Set}\left(\rho_{1:N_R}^{l+1}(t), \sum_{1:M}^{l+1}\right) = \left(\rho_{1:N_R}^l(t), \sum_{1:M}^l\right) + \frac{\alpha}{2}H_l\nabla g_k\left(\rho_{1:N_R}^l(t), \sum_{1:M}^l\right) + \mathcal{N}(0, \alpha H_l)$ 3. If $(l+1)\bmod L_0 = 0$, then set $\alpha = \frac{\alpha}{2}$ The matrix $H_l$ is the so-called preconditioner which, for regional inversions according to this embodiment, is the RMSProp preconditioner. The scalar $\alpha$ is the learning rate which is decreased by half every $L_0$ iterations. The random vector $\mathcal{N}(0, \alpha H_l)$ is drawn from the zero-mean, multivariate normal distribution with covariance $\alpha H_l$. FIG. 6 shows samples of emission rate associated with a single emitter generated by a regional inversion and the resulting empirical posterior distribution of emission rate. The line plot at the top of FIG. 6 shows samples of emission rate generated by a regional inversion according to this embodiment. The histogram at the bottom of FIG. 6 shows the corresponding empirical posterior distribution of emission rate generated according to this embodiment.

Schematic Data Flow for Regional Inversions

Figure 7:
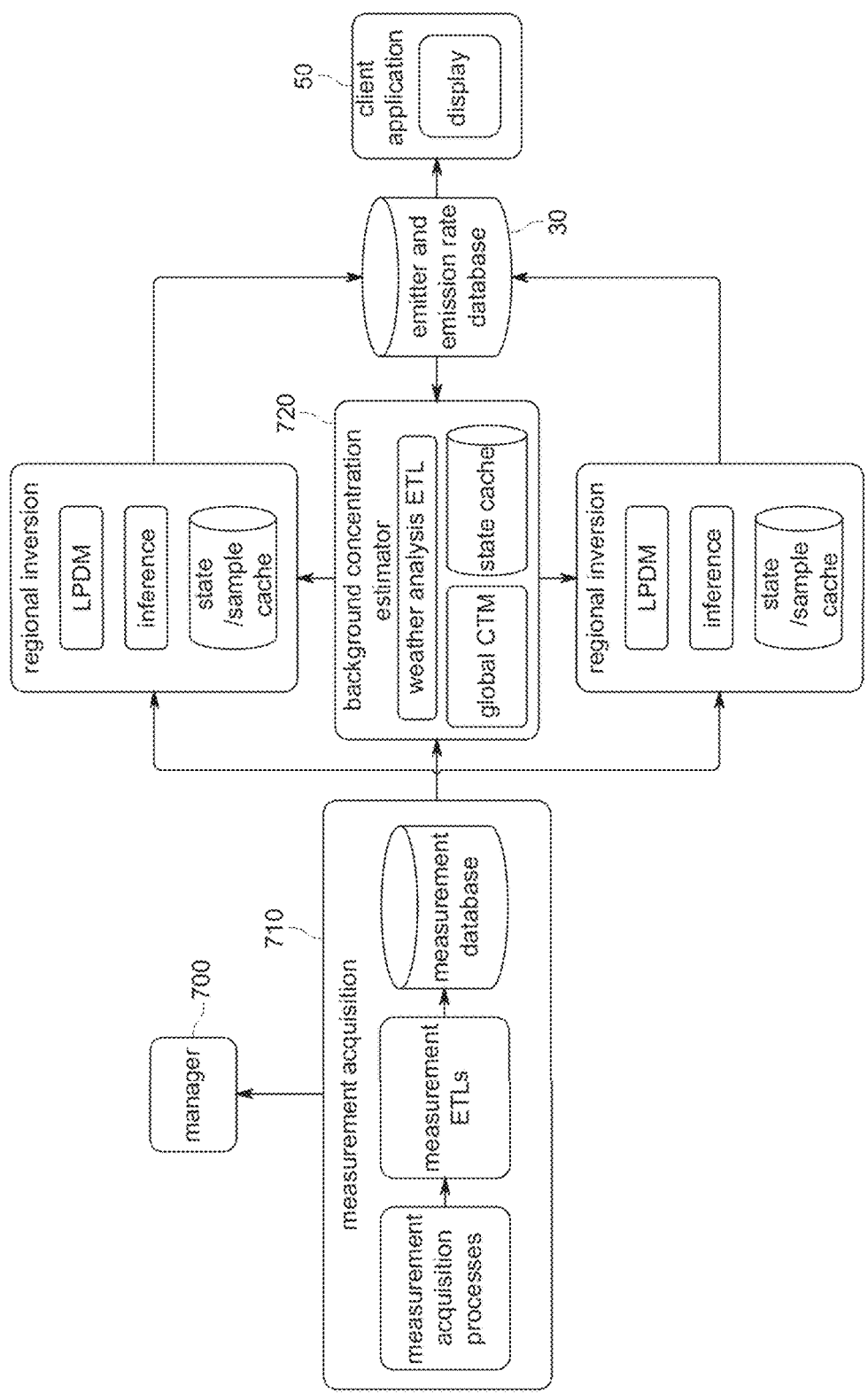
FIG. 7 is a schematic data flow diagram showing data flows according to an implementation of the invention.

FIG. 7 is a schematic data flow diagram showing data flows and components used in an embodiment of the invention that determines a probabilistic distribution of global atmospheric gases using a 'regional inversion'-based model as described above. As would be clear, various components of FIG. 7 may be implemented by the server 20 of the system described above and/or by the processor 40.

The manager module 700 in FIG. 7 coordinates data acquisition and execution of regional inversions and generation of background concentration fields, and is connected with the measurement acquisition module 710. The measurement acquisition module 710 acquires and stores column averaged GHG concentration measurements. As described above, measurement data may be obtained in any suitable way (e.g., directly from real-time or near-real-time sensors; from internal or external data stores, etc.) and may undergo preprocessing steps (although such preprocessing steps are not necessarily required).

The measurement acquisition module 710 passes data to the background concentration estimator module 720, which acquires weather analysis data and runs the global CTM to generate column averaged background GHG concentration fields. Data from the measurement acquisition module 710 is also used to run regional inversions 730A and 730B. Of course, it would be understood that this diagram shows only two regional inversions for simplicity, but that any suitable number of regional inversions may be performed by the system described herein.

Data records from the inversions, as well as other data related to potential emitters and associated emissions, can then be stored in the database 30. The data in the database 30 can also be used for estimates and calculations by the background concentration estimator module 720. Stored information, visual representations, data, etc., can then be passed to a display module 50 or other internal or external application, as described above.

In some embodiments, the measurement acquisition module 710 and the display 50/further application can be autonomous from the rest of the system. For example, the measurement acquisition module 710 can be a third-party data source with which the manager module 700 and/or the server 20 communicates. The remaining components shown in FIG. 7 (i.e., the background concentration estimator module 720 and the regional inversions 730) can be coordinated by the manager and are, in preferable embodiments, run in a perpetual loop. Each iteration of the loop represents the passage of $\Delta t$ units of real time. System behaviour at each iteration of the loop is as follows:

1. The manager module 700 checks a measurement database associated with the measurement acquisition module 710 for new column averaged GHG concentration measurements;
2. If there are new measurements, for each region that intersects measurement pixels, the manager module 700 runs the associated regional inversion 730;
3. For each regional inversion that is run,
    a. The manager module 700 queries the background concentration estimator module 720 for the most recently updated background concentration estimates;
    b. The manager module 700 queries the measurement database for new column averaged GHG concentration measurements;
    c. The manager module 700 directs the execution the regional inversion; and
    d. Emission rate estimates resulting from the regional inversion are added to the database 30; and
4. The manager module 700 runs the background concentration estimator module 720 to generate new background concentration estimates using the new data from the regional inversion(s).

In a preferred embodiment, the server 20 and processor 40 (and each of the above identified modules) is implemented to run in a distributed (e.g., cloud-based) and asynchronous manner, coordinated by the manager module 700. There may thus be any suitable number of instantiated versions of the system operating at any given time.

The database 30 stores records for each potential GHG emitter in the set E. This record stores the emitter's location and other metadata, such as the emitter's type (e.g., oil well, termite mound, etc.) and its owner or operator (if applicable, i.e., if the emitter is an anthropogenic source of GHG). Associated with each emitter record is a sequence of records that store emission rate summaries. Such a record is preferably added to the database 30 whenever an emission rate is estimated for the emitter. Of course, depending on the implementation, the database 30 may be updated continuously or near-continuously or may receive batch updates at discrete and/or predetermined intervals.

It is inefficient to store full emission rate estimates, i.e., full empirical approximations of the posterior distribution of emission rate given column averaged GHG concentration measurements. Thus, for any emission rate estimate, a lognormal distribution is fit to the emission rate samples that realise the estimate. The scale and location parameters of the lognormal summarise the emission rate estimate and are added to the database 30.

Figure 8:
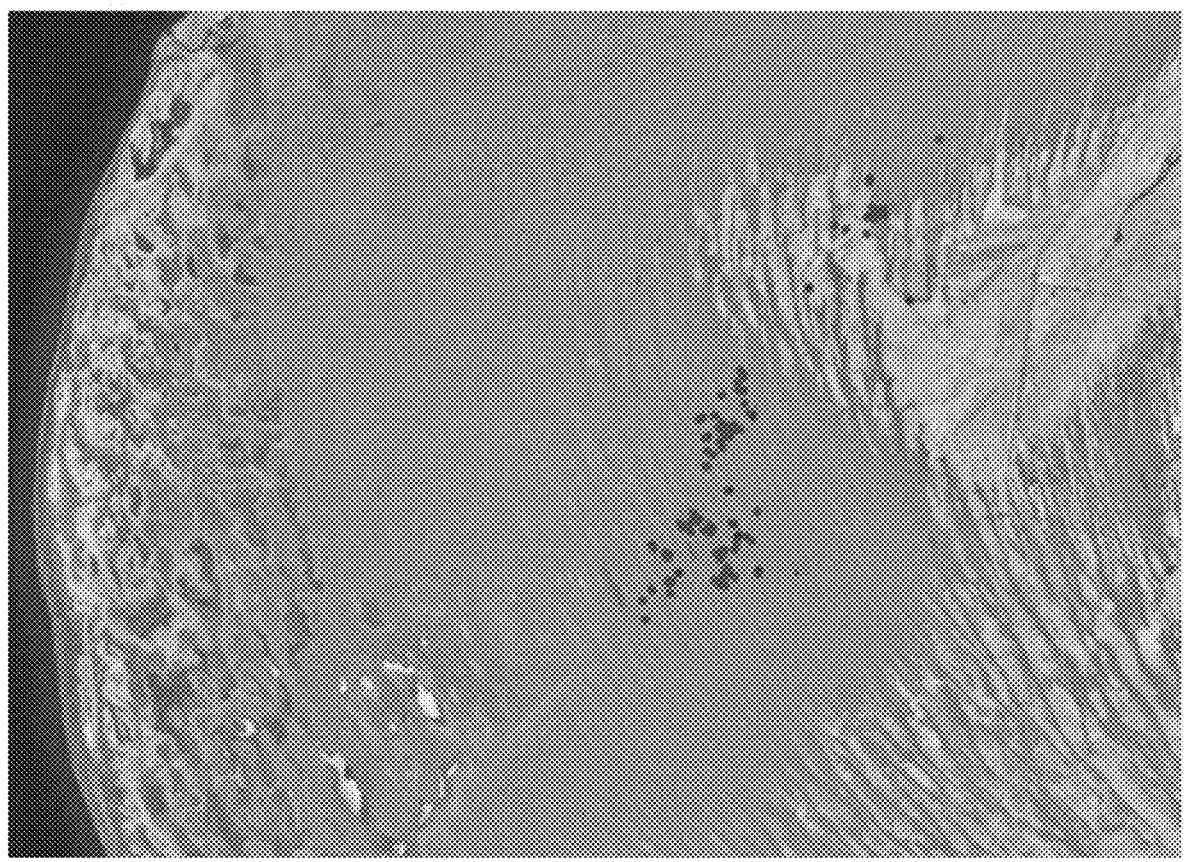
FIG. 8 shows an exemplary display image according to an embodiment of the invention.
Figure 9:
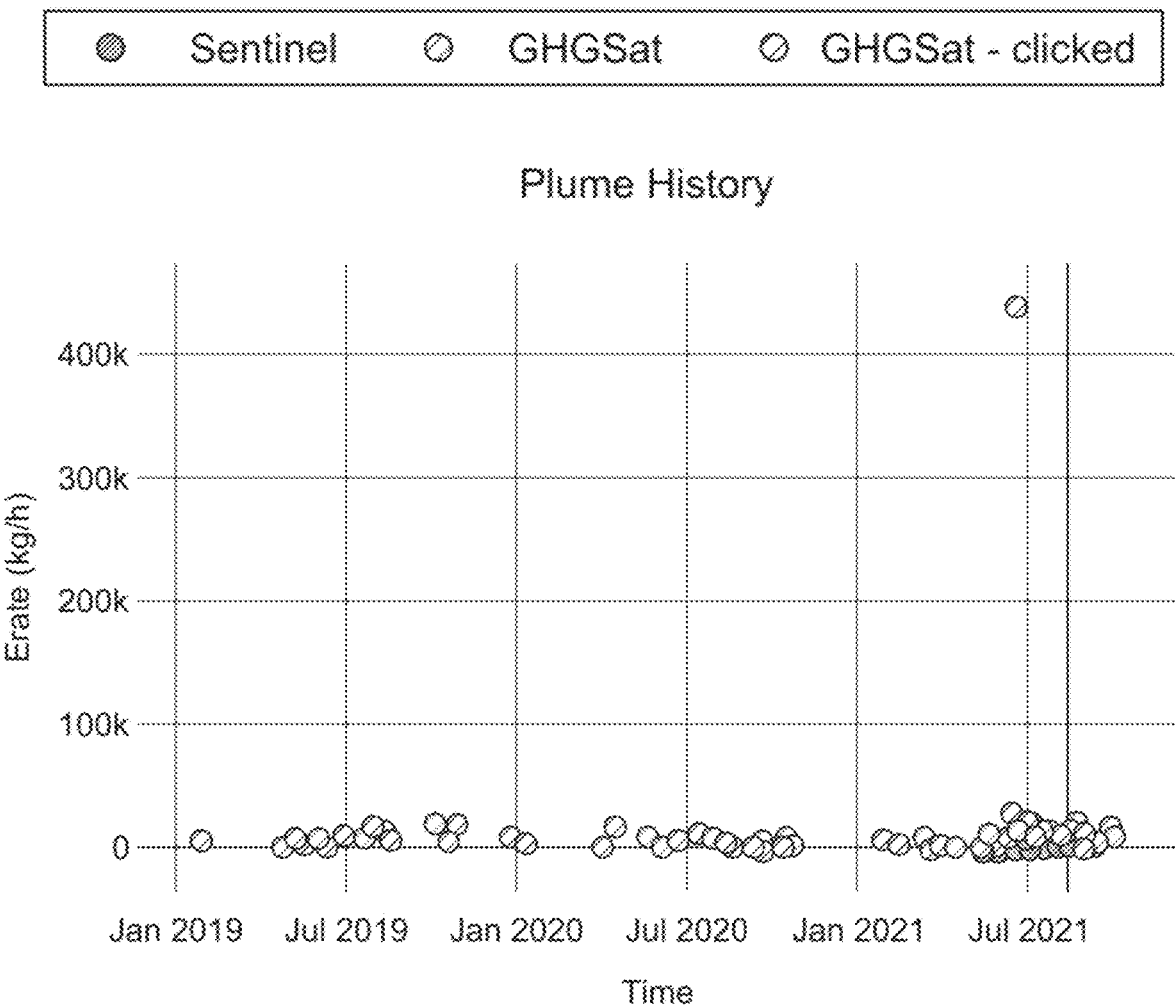
FIG. 9 shows another exemplary display image according to an embodiment of the invention.

FIGS. 8 and 9 show exemplary images that can be provided to a user through a display 50. FIG. 8 shows emitters and emissions (as determined by the regional inversion-based embodiment described above) on a map. Each blue dot represents the location of a potential GHG emitter. Each purple dot represents the location of an emission. As can be seen, there are more emissions than emitters in this exemplary region, and the various emissions have, in many cases, moved away from the specific geographic location of emitters.

FIG. 9 shows a time series of emission rates for a specific exemplary emitter selected by the user. The time series points are the modes of the lognormal summaries of emission rate. This specific data can be used to analyse the particular emissions of individual emitters/emission sites with high temporal and spatial resolution.

Another possible type of display 50 can aggregate emission rate summaries on a grid over a user-specified period of time. For example, suppose a regular grid is imposed on a given region. For each of the grid cells, a corresponding colour can be determined, representing the sum of emission rates estimated in the cell over the given period of time, i.e., to provide a "heatmap" scheme. The resulting coloured grid can be displayed to the user.

Figure 10:
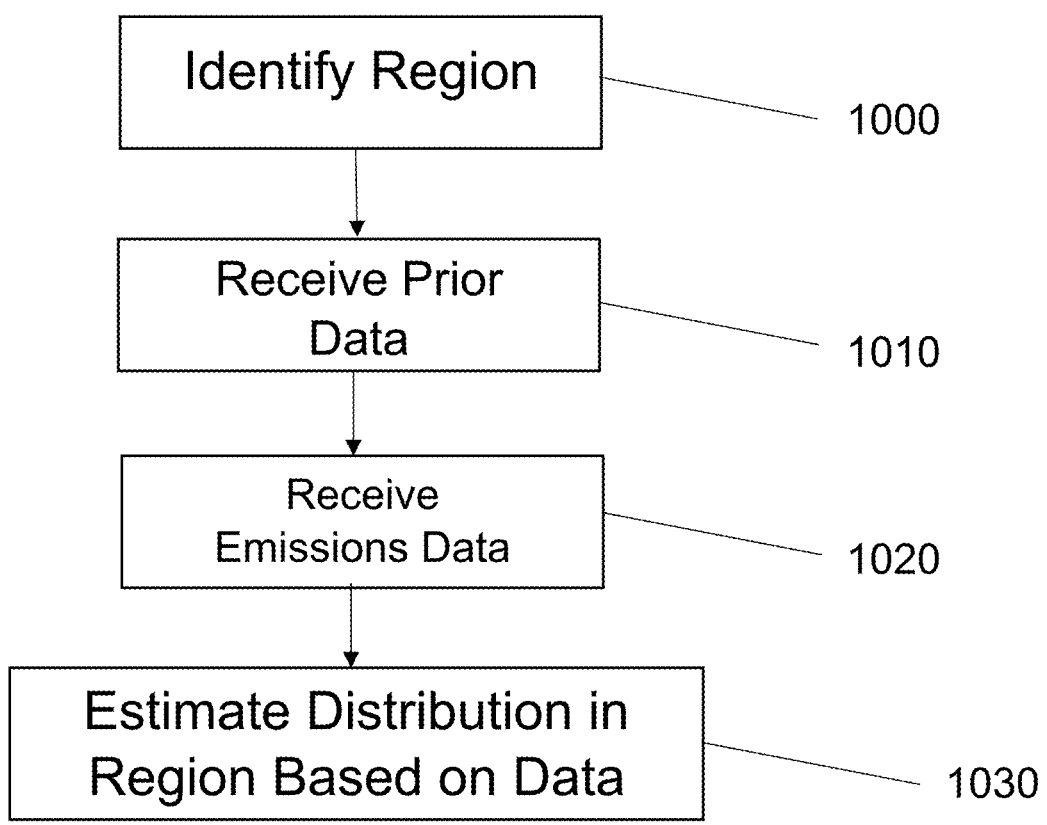
FIG. 10 is a flowchart detailing a method according to one aspect of the invention.

Referring now to FIG. 10, a flowchart detailing a method according to an aspect of the invention is shown. At step 1000, a specific region is identified. At step 1010, prior data (which can comprise data related to prior probability distribution(s), prior concentration(s), prior trend(s), and/or prior emission rate(s), either globally or specific to the specific region) are received. At step 1020, emission data related to emissions in the specific region are received. (Again, as should be clear, current concentration data may also be provided.) At step 1030, the probability distribution of the gas in that specific region is estimated based on the prior data and on the emission data. As would be clear, steps 1010 and 1020 may be performed in any order, and, in some cases, may be ongoing processes allowing continual updating of the estimated distribution. As discussed above, in some embodiments, the entire surface of the Earth is represented as a grid comprising numerous grid cells (each a region), and the above method is performed for every grid cell, to thereby produce an estimated distribution for the entire atmosphere.

As would also be clear, the mathematical models and data sources used may be adjusted by human operators and/or by algorithmic check/correction processes to reduce error, prevent model drift, and/or more accurately reflect real-world conditions.

The various aspects of the present invention may be incorporated into numerous implementations and embodiments that allow for various capabilities and analyses. As examples, the various aspects of the present invention may be used to enable the continuous quantification of gas emissions inventories at any geographic scale (local, province/state, national, etc.). As well, the various aspects of the present invention will provide a higher-resolution and higher-frequency model of three-dimensional gas concentrations globally. This model can, in turn, enable a better understanding of gas impact on local and regional health, climate, and even weather. On a more practical side, the various aspects of the present invention enables detection of gas emissions hotspots. The detection of such hotspots can, in turn, lead to attribution of emissions to specific sources, leading to improved mitigation efforts. The various aspects of the present invention also enables modelling of changes in gas concentrations and emissions inventories due to changes in emissions sources, such as changing coal production or changing oil and gas production each in specific locations/regions.

It should be clear that the various aspects of the present invention may be implemented as software modules in an overall software system. As such, the present invention may thus take the form of computer executable instructions that, when executed, implements various software modules with predefined functions.

The embodiments of the invention may be executed by a computer processor or similar device programmed in the manner of method steps, or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language. For example, preferred embodiments may be implemented in a procedural programming language (e.g., "C" or "Go") or an object-oriented language (e.g., "C++", "java", "PHP", "PYTHON" or "C#"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A computer implemented method for estimating how a gas is distributed in a geospatial region, the method comprising:
    identifying a specific region of the Earth's surface;
    receiving prior data, wherein said prior data is related to at least one of: how said gas was previously distributed, a prior concentration, a prior trend, and a prior emission rate for said gas in said specific region;
    receiving emission data from at least one sensor in said specific region, wherein said emission data is related to an emission rate of said gas is said specific region;
    based on said prior data and said emission data, estimating an inward flow of said gas into said specific region and an outward flow of said gas from said specific region and estimating a probability distribution for said gas within said specific region; and
    displaying, on a display, a visual representation of said probability distribution as an overlay on a map projection,
wherein said specific region has a length of 0.025° and a width of 0.025°.

2. The method according to claim 1, wherein said distribution is estimated using at least one statistical inference technique.

3. The method according to claim 1, wherein said distribution is estimated using a combination of statistical techniques.

4. The method according to claim 3, wherein said statistical techniques are selected from a group consisting of: a particle dispersion model; a Lagrangian particle dispersion model (LPDM); a chemical transport model (CTM); a global chemical transport model; an inversion technique; and a regional inversion technique.

5. The method according to claim 4, wherein said inward flow and said outward flow are accounted for when estimating said probability distribution.

6. The method according to claim 1, wherein said specific region is determined based on an equirectangular projection of the Earth's surface.

7. The method according to claim 5, wherein said method is performed for every region in said equirectangular projection, to thereby produce estimates of how said gas is distributed over the atmosphere.

8. The method according to claim 1, wherein said probability distribution is updated in at least one of real time and near real time.

9. The method according to claim 1, wherein said gas is methane.

10. The method according to claim 1, wherein said step of estimating said probability distribution is also based on a current concentration measurement of said gas within said specific region, wherein said current concentration measurement is obtained in at least one of real time and near real time.

11. The method according to claim 1, wherein said method is implementable by executing computer-readable and computer-executable instructions encoded on non-transitory computer-readable media.

12. The method according to claim 1, further comprising the steps of:
    receiving input from a user, said input being related to a change in conditions in said specific region;
    modeling estimated effects of said change in conditions on said probability distribution, said inward flow of gas, and said outward flow of gas; and
    updating said visual representation to include said estimated effects, such that said display displays an updated visual representation.

13. A system for estimating how a gas is distributed in a geospatial region, said system comprising:
    at least one sensor disposed in said geospatial region, said at least one sensor being for gathering emission data;
    a server for:
        receiving prior data, wherein said prior data is related to at least one of how said gas was previously distributed, a prior concentration, a prior trend, and a prior emission rate for said gas in said specific geospatial region; and
        receiving said emission data from said at least one sensor, wherein said emission data is related to an emission rate of said gas in said specific region;
    at least one processor for estimating an inward flow of said gas into said geospatial region and an outward flow of said gas from said geospatial region and for estimating a probability distribution for said geospatial region based on said prior data and said emission data and for generating a visual representation for said probability distribution;
    a database for storing said prior data, said emission data, said probability distribution, said inward flow of said gas, and said outward flow of said gas,
    a display for displaying to a user said visual representation as an overlay on a map projection,
wherein said geospatial region has a length of 0.025° and a width of 0.025°.

14. The system according to claim 13, wherein said probability distribution is estimated using at least one statistical inference technique.

15. The system according to claim 13, wherein said probability distribution is estimated using a combination of statistical techniques.

16. The system according to claim 15, wherein said statistical techniques are selected from a group consisting of: a particle dispersion model; a Lagrangian particle dispersion model (LPDM); a chemical transport model (CTM); a global chemical transport model; an inversion technique; and a regional inversion technique.

17. The system according to claim 13, wherein said inward flow and said outward flow are accounted for when estimating said probability distribution.

18. The system according to claim 13, wherein said geospatial region is determined based on an equirectangular projection of the Earth's surface.

19. The system according to claim 18, wherein said method is performed for every region in said equirectangular projection, to thereby produce distribution estimates for said gas over the atmosphere.

20. The system according to claim 13, wherein said distribution is updated in at least one of real time and near real time.

21. The system according to claim 13, wherein said gas is methane.

22. The system according to claim 13, wherein said user interacts with said display.

23. The system according to claim 19, wherein said user interacts with said display.

24. The system according to claim 13, wherein said probability distribution is further based on a current concentration measurement of said gas within said geospatial region, wherein said current concentration measurement is obtained in at least one of real time and near real time.

25. The system according to claim 13, wherein said user provides input to said system, said input being related to a change in conditions in said specific region, wherein said processor is further for modeling estimated effects of said change in conditions on said probability distribution, said inward flow of gas, and said outward flow of gas, and wherein said visual representation is updated to include said estimated effects, such that said visual representation displayed on said display illustrates said estimated effects.

* * * * *